(12) United States Patent
Kern et al.

(10) Patent No.: US 6,318,332 B1
(45) Date of Patent: Nov. 20, 2001

(54) METHOD FOR MONITORING ADEQUATE OIL LUBRICATION OF AN INTERNAL COMBUSTION ENGINE AND AN INTERNAL COMBUSTION ENGINE FOR CARRYING OUT THE METHOD

(75) Inventors: Eckhart Kern; Werner Wallrafen, both of Hofheim; Joachim Acht, Frankfurt; Volker Wehrmeyer, Königstein, all of (DE)

(73) Assignee: Mannesmann VDO AG (DE)

( * ) Notice: Subject to any disclaimer, the term of this patent is extended or adjusted under 35 U.S.C. 154(b) by 0 days.

(21) Appl. No.: 09/461,789

(22) Filed: Dec. 15, 1999

(30) Foreign Application Priority Data

Dec. 22, 1998 (DE) ................................ 198 59 337

(51) Int. Cl.[7] .................................................... F01M 11/10

(52) U.S. Cl. .................................... 123/196 S; 123/196 R

(58) Field of Search ............................ 123/196 S, 196 R; 184/6.4, 6.23

(56) References Cited

U.S. PATENT DOCUMENTS

| 4,599,888 | | 7/1986 | Hufton, et al. . | |
|---|---|---|---|---|
| 4,859,864 | * | 8/1989 | Smith | 250/577 |
| 4,913,108 | | 4/1990 | Sougawa, et al. . | |
| 5,326,447 | * | 7/1994 | Fletcher | 204/401 |
| 5,814,214 | * | 9/1998 | Chun | 210/130 |
| 5,922,969 | * | 7/1999 | Haar | 73/861.02 |

FOREIGN PATENT DOCUMENTS

| 3931497A1 | 9/1989 | (DE) . |
|---|---|---|
| 0039244A1 | 4/1981 | (EP) . |
| 0816839A1 | 6/1997 | (EP) . |

* cited by examiner

Primary Examiner—Willis R. Wolfe
Assistant Examiner—Jason Benton
(74) Attorney, Agent, or Firm—David M. Thimmig; Mayer, Brown & Platt

(57) ABSTRACT

To monitor adequate oil lubrication of an internal combustion engine, air bubbles in the oil flow are detected by means of a sensor arranged in an oil line of a pressure circulation lubrication system and connected to an electronic evaluation system. These air bubbles are an early indicator of inadequate lubrication of the internal combustion engine.

42 Claims, 2 Drawing Sheets

METHOD FOR MONITORING ADEQUATE OIL LUBRICATION OF AN INTERNAL COMBUSTION ENGINE AND AN INTERNAL COMBUSTION ENGINE FOR CARRYING OUT THE METHOD

BACKGROUND OF THE INVENTION

The invention relates to a method for monitoring adequate oil lubrication of an internal combustion engine, in particular that of a vehicle, by means of a sensor arranged in an oil line of a pressure circulation lubrication system and connected to an electronic evaluation system. The invention also relates to an internal combustion engine for carrying out this method.

Proper functioning of the pressure circulation lubrication system is of decisive importance to the service life of internal combustion engines. If the oil film on the cylinder walls breaks down, the engine overheats very rapidly and this rapidly leads to serious engine damage. Currently, adequate oil lubrication of internal combustion engines is monitored only indirectly by sensors which measure the pressure in the oil line. If the pressure falls due, for example, to failure of the oil pump or a leak in the oil circuit, the driver receives a warning signal. In addition, the oil level in the oil pan is often monitored by means of a sensor in order to ensure that there is always a sufficiently large supply of oil.

It has been found in practice, however, that an oil pressure drop can often only be detected when serious engine damage has already occurred due to inadequate lubrication. Monitoring the oil level in the oil pan does not ensure an adequate oil supply either. Owing to dynamic driving states, e.g. when driving round a relatively long bend, when driving on a slope or during acceleration, the oil level in the oil pan can shift to such an extent that the oil pump draws in air instead of oil and, as a result, lubrication temporarily ceases and inadequate lubrication occurs.

The problem underlying the invention is to develop a method for monitoring adequate oil lubrication of an internal combustion engine by means of which a warning can be given as early as possible if there is a risk of inadequate engine lubrication. The intention is furthermore to develop an internal combustion engine which operates in accordance with such a method.

SUMMARY OF THE INVENTION

According to the invention, the first-mentioned problem is solved by virtue of the fact that gas bubbles in the oil flow of the oil line are detected by means of the sensor and the electronic evaluation system.

By means of such a method, it is possible to generate a warning even if air is temporarily being drawn in with the oil owing to dynamic driving states or if very slight leaks, through which air enters the system, occur in the intake region of the oil circuit. The risk of inadequate engine lubrication is thereby detected in good time. A warning signal can be generated even before engine lubrication ceases. The method according to the invention is not limited to use with motor vehicles. The risk that air will be drawn in owing to dynamic traveling states is very great in the case of ships, for example, when large waves occur, or in the case of sailing ships operating simultaneously under engine power and under sail because the sails can often lead to a pronounced and prolonged tilt. With motorized aircraft too, there is the risk of an inadequate supply of lubricant due to dynamic flying states.

The further away the sensor is from the lubrication points of the internal combustion engine, the earlier a warning signal can be generated when there is a risk of inadequate engine lubrication. It is therefore advantageous if the sensor is arranged in an oil intake line upstream of an oil pump of the pressure circulation lubrication system.

If a somewhat lower detector speed—i.e. a shorter time between detection and the arrival of the bubbles in the cylinders of the engine—is acceptable, it is, however, also possible for the sensor to be arranged downstream of the oil pump and downstream of an oil filter arranged downstream of the oil pump. This has the advantage that the sensor responds even to air bubbles which enter the oil flow upstream of the sensor owing to leaks in the oil filter or, for example, the oil line.

The sensor for detecting air bubbles can vary widely in design. It would be possible, for example, to monitor the translucence of the oil flow with an optical sensor. The sensor is of particularly simple configuration if a sensor operating on the thermoelectric principle is used. Such sensors are already common for level monitoring and can therefore be obtained at relatively low cost. The sensor is of simple construction and is therefore particularly suitable for large-scale manufacture if, as is advantageous, it has a temperature-dependent wire resistor. The operational reliability and durability of the sensor is particularly high if, as is preferred, it has a thermistor.

It is likewise possible to resort to sensors commonly used for level monitoring if, in accordance with another development of the method according to the invention, a capacitive sensor is used as a sensor to detect changes in the dielectric constant of the oil flow passing the sensor.

A particularly advantageous development of the method consists in the sensor being arranged at the level of the minimum permissible oil level in an oil pan of the internal combustion engine, and the electronic evaluation system being used to detect when the oil level in the oil pan falls below the minimum with the internal combustion engine stationary, in addition to detecting bubbles with the internal combustion engine running. This allows the sensor to be used for a dual purpose, namely, on the one hand, to monitor engine lubrication with the internal combustion engine running and, on the other hand, to monitor the oil level with the internal combustion engine stationary.

To determine a filling level and the presence of air bubbles, it is advantageous if a constant current is allowed to flow through the resistance body for a defined period of time for each measurement of the oil level, and the voltage drop at the beginning and the end of energization is determined.

For continuous monitoring of an oil flow with regard to the presence of bubbles, it is advantageous if a constant current is allowed to flow through the resistance body for the continuous detection of bubbles, and at the same time the signal fluctuations of the voltage are determined for the purpose of ascertaining the concentration of gas bubbles.

It is also possible to use a mechanically operating sensor for the method according to the invention if a sensor operating with a dynamic pressure flap which can be deflected by the oil flow is used as the sensor. Here, use is made of the fact that the inertia forces acting on the dynamic pressure flap are lower due to air bubbles in the oil flow, with the result that the flap is then deflected to different degrees.

A sensor of relatively low accuracy of response is sufficient if the sensor is arranged above an approximately horizontal region of the oil line, in the upper region of a flow stagnation space connected in the lower region to the oil line. This gives rise to an integrating effect. Small air bubbles which occur in the oil circuit and which, taken by themselves, would not trigger a warning signal collect in the flow stagnation space. Once the amount of air collected there is such that the sensor is no longer immersed in oil, said sensor triggers a warning signal.

The air collecting in the flow stagnation space flows slowly back into the oil circuit and, if air bubbles do not continue to occur, the sensor is thus reimmersed in oil and becomes operational as a result if, in accordance with another development of the method, the flow stagnation space is connected to the oil line via a large cross section in the lower region and, in its upper region, is connected to the oil line in a region of relatively low pressure via a smaller cross section.

The second problem mentioned, namely the provision of an internal combustion engine operating by the method according to the invention, is solved, in accordance with the invention, if the sensor and the electronic evaluation system are designed to detect gas bubbles in the oil flow of the oil line. In the case of such an engine, a warning can be output even before inadequate oil lubrication occurs, i.e. as soon as there is a threat of such a state.

A particularly early warning is obtained if the sensor is arranged in an oil intake line upstream of an oil pump of the pressure circulation lubrication system.

It is also possible to detect leaks in the region of the oil filter and the oil pump if the sensor is arranged downstream of the oil pump and downstream of an oil filter arranged downstream of the oil pump.

The sensor is of particularly simple configuration if the sensor is a sensor operating on the thermoelectric principle. A particularly simple and low-cost sensor is obtained if it has a temperature-dependent wire resistor. The sensor is very reliable even over a long period of operation if, as is advantageous, it has a thermistor.

A sensor design of comparable simplicity can be obtained if the sensor is a capacitive sensor for detecting changes in the dielectric constant of the oil flow passing the sensor.

The sensor can perform a dual function if it is arranged at the level of the minimum permissible oil level in an oil pan of the internal combustion engine, and the electronic evaluation system is designed to detect when the oil level in the oil pan falls below the minimum with the internal combustion engine stationary, in addition to detecting bubbles with the internal combustion engine running.

The sensor can be used to measure not only when the oil level falls below a minimum but even to measure the particular oil level if, in accordance with another development of the invention, the sensor and the electronic evaluation system are designed to detect gas bubbles in the oil flow with the internal combustion engine running and to detect the oil level with the internal combustion engine stationary.

The sensor can also be a mechanically operating component if the sensor has a dynamic pressure flap which can be deflected by the oil flow.

If very small air bubbles that cannot be detected by the sensor occur, these can first of all be collected and, when a defined quantity of air bubbles has been exceeded, can generate a warning signal if, in accordance with another refinement of the invention, the sensor is arranged above an approximately horizontal region of the oil line, in the upper region of a flow stagnation space connected in the lower region to the oil line.

The air which collects in the flow stagnation space is automatically guided back into the oil circuit if the flow stagnation space is connected to the oil line via a large cross section in the lower region and there is a connection from its upper region to the oil line in a region at relatively low pressure via a smaller cross section.

Whatever the cross-sectional regions in which air bubbles occur, they can be detected by the sensor according to the invention if, at one level, the sensor has a resistance wire which extends in a meander shape over the cross section of the oil line.

It is to be understood that both the foregoing general description and the following detailed description are exemplary and provided for purposes of explanation only, and are not restrictive of the invention as claimed.

BRIEF DESCRIPTION OF THE DRAWINGS

The invention allows for various embodiments. To further clarify its basic principle, a number of these are illustrated in the drawing and described below. In the drawing.

It should be understood that the present invention is not limited to the preferred embodiments illustrated.

DETAILED DESCRIPTION OF THE PREFERRED EMBODIMENTS

Referring generally to FIGS. 1 through 9, it will be appreciated that the present invention may be embodied in numerous configurations.

Figure 1:
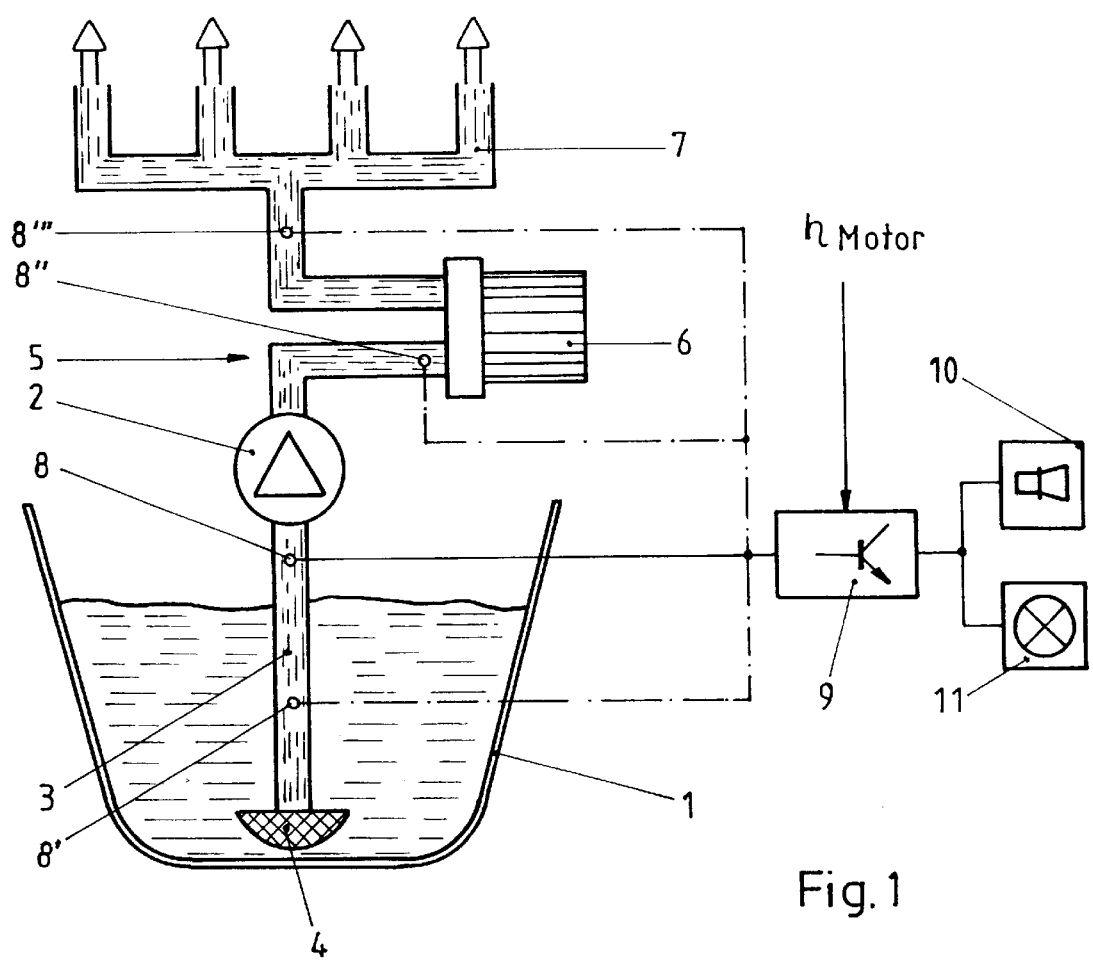
FIG. 1 shows a diagrammatic sketch of pressure circulation lubrication in accordance with the method according to the invention.

FIG. 1 shows an oil pan 1 of an internal combustion engine, from which oil is drawn by means of an oil pump 2. For this purpose, the oil pump 2 is inserted into an oil line 5 which projects into the oil pan 1 by means of a vertically arranged oil intake line 3 with an intake filter 4 mounted close to the bottom of the oil pan 1. From the oil pump 2, the oil line 5 leads to an oil filter 6 and, from there, to an oil distributor 7.

Arranged in the oil intake line 3 is a sensor 8 for monitoring air bubbles which arise there while the internal combustion engine is running. This sensor 8 is connected to an electronic evaluation system 9 which is capable of activating a tone generator 10 or a warning lamp 11 for the purpose of generating a warning signal. FIG. 1 shows three further possibilities for the mounting of the sensor 8, these being shown in chain-dotted lines. 8' indicates the arrangement of a sensor at the minimum oil level, 8" a mounting point directly upstream of the oil filter 6, and 8''' a mounting point for the sensor upstream of the oil distributor. If the sensor 8 is arranged at position 8' at a level of the minimum permissible oil level, the following functional enhancement is obtained: if the sensor is energized when the engine is stationary, it is possible to ascertain, by determining the voltage drop, whether it is immersed in oil or is above the oil level, in air, because, in the latter case, it is cooled less. It is possible in this way to obtain a signal which indicates when a minimum oil flow is undershot with the internal combustion engine stationary.

Figures 2, 3, 4:
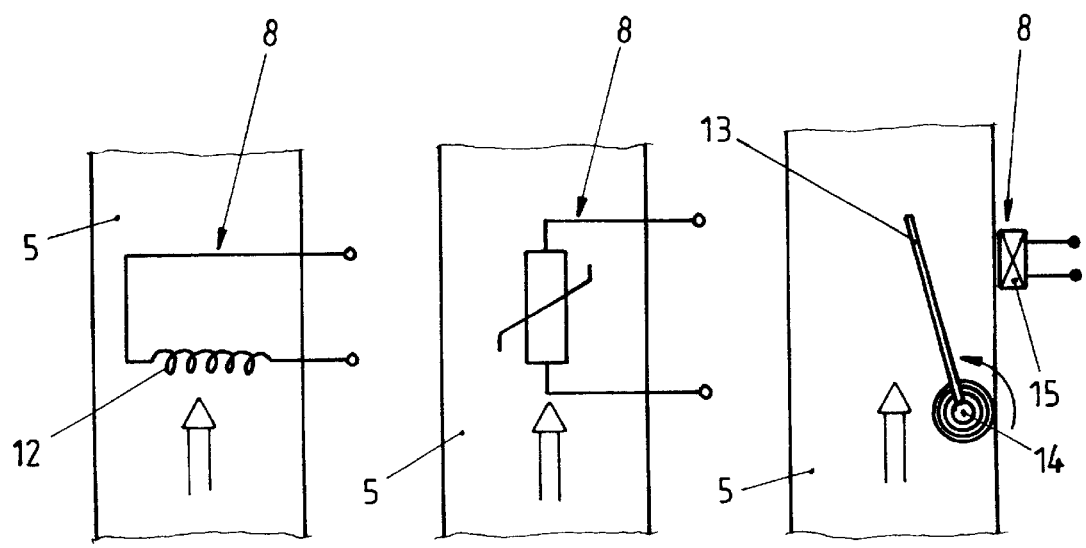
FIG. 2 shows a sensor in an oil line, said sensor operating on the thermoelectric principle on the basis of a resistance wire.
FIG. 3 shows a sensor in an oil line, said sensor operating on the thermoelectric principle on the basis of a thermistor.
FIG. 4 shows a sensor in an oil line, said sensor operating mechanically on the basis of a dynamic pressure flap.

The sensor 8 shown in FIG. 2 operates on the thermoelectric principle. It has a resistance body 12, which is designed as a wire and is arranged in the oil flow in the oil line 5. This resistance body 12 is energized periodically with a constant current, as a result of which the resistance body 12 heats up. The resulting change in the voltage drop is measured. If gas bubbles, in particular air bubbles, occur in the oil flow, the resistance body 12 is cooled less and this can be detected from the change in the voltage drop. As an alternative intended for continuous air-bubble detection, a constant current can flow through the resistance body and the signal fluctuations of the voltage across the resistance body can be evaluated to ascertain the concentration of air bubbles. This can be accomplished, for example, by bandpass filtering or a microprocessor with a suitable evaluation algorithm.

FIG. 3 shows a sensor 8 in the oil line 5, said sensor being designed as a thermistor.

The sensor 8 shown in FIG. 4 has a dynamic pressure flap 13 which is arranged in such a way as to be pivotable about a horizontal axis 14 and is moved upwards in the drawing by the oil flow. A position sensor 15 monitors the position of the dynamic pressure flap 13. If there are air bubbles in the oil flow, the dynamic pressure flap 13 is deflected upwards to a lesser extent than that shown in FIG. 4, enabling the position sensor 15 to generate a corresponding signal.

Figure 5:
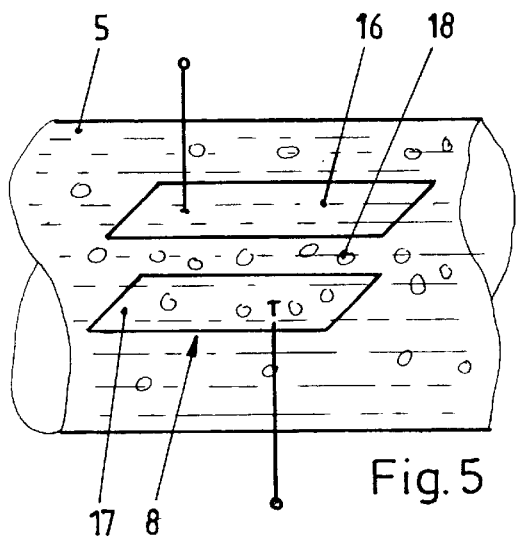
FIG. 5 shows a sensor in an oil line, said sensor operating on the capacitive principle on the basis of two plates.
Figure 6:
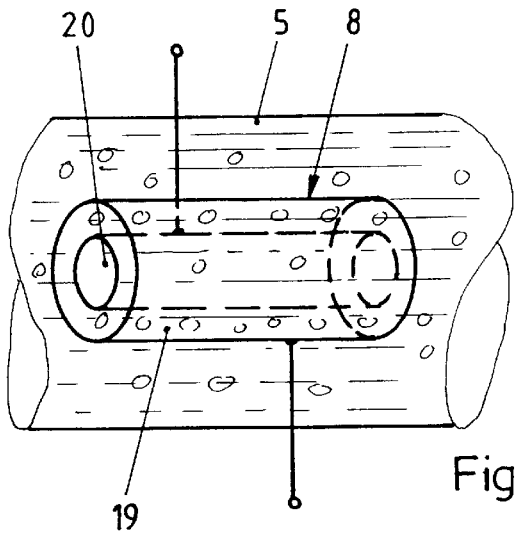
FIG. 6 shows a sensor operating on the capacitive principle on a coaxial basis.

In FIGS. 5 and 6, the sensors 8 are each designed as capacitors. FIG. 5 shows two capacitor plates 16, 17, between which a certain portion of the oil flow moves. If there are air bubbles 8 in the oil flow, the dielectric constant of the medium changes, leading to a change in the capacitance of the capacitor.

The embodiment shown in FIG. 6 differs from that in FIG. 5 only in terms of its construction in that the two capacitor plates 16, 17 are replaced by two coaxial tubes 19, 20.

Figure 7:
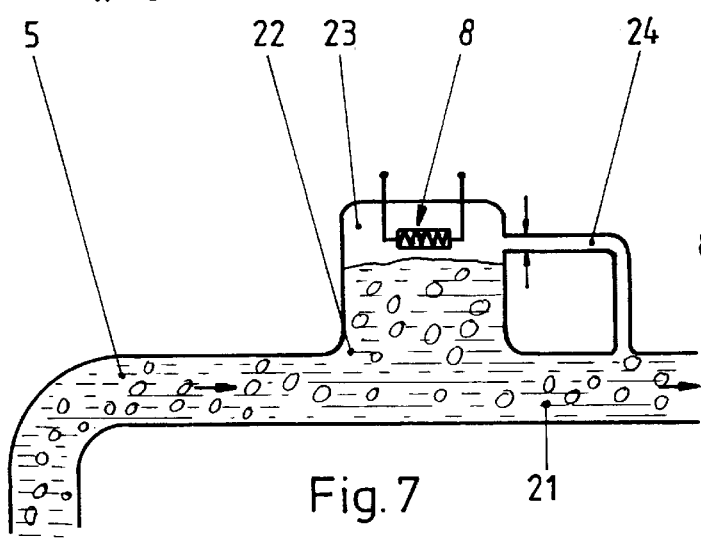
FIG. 7 shows an arrangement of a sensor in an oil line configured specially for this purpose with an integrating effect.

FIG. 7 shows a horizontal region 21 of the oil line with an upward-oriented, pot-shaped projection 22 which forms a flow stagnation space 23. The sensor 8 is arranged at the top of this flow stagnation space 23. A connection 24 leads back from the upper region of the flow stagnation space 23 to the region 21 of the oil line at a point where the pressure is lower than in the region of the projection 22. This connection 24 has a smaller cross section than the projection 22. As a result, air collects more rapidly in the projection 22 than it can leave it again and, if there is a relatively large number of air bubbles, the sensor 8 is thus outside the oil within a short time and therefore heats up and triggers a warning signal.

Figure 8:
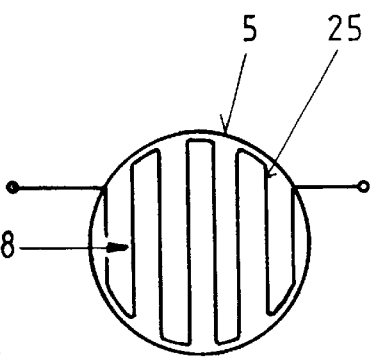
FIG. 8 shows a cross section through the oil line in the region of a sensor.

In the embodiment shown in FIG. 8, the sensor 8 is formed by a resistance wire 25 which extends in a meander shape over the entire cross section of the oil line 5. This ensures that a high proportion of the air bubbles which occur in the oil flow come into contact with the resistance wire 25 and in this way influence the sensor 8.

Figure 9:
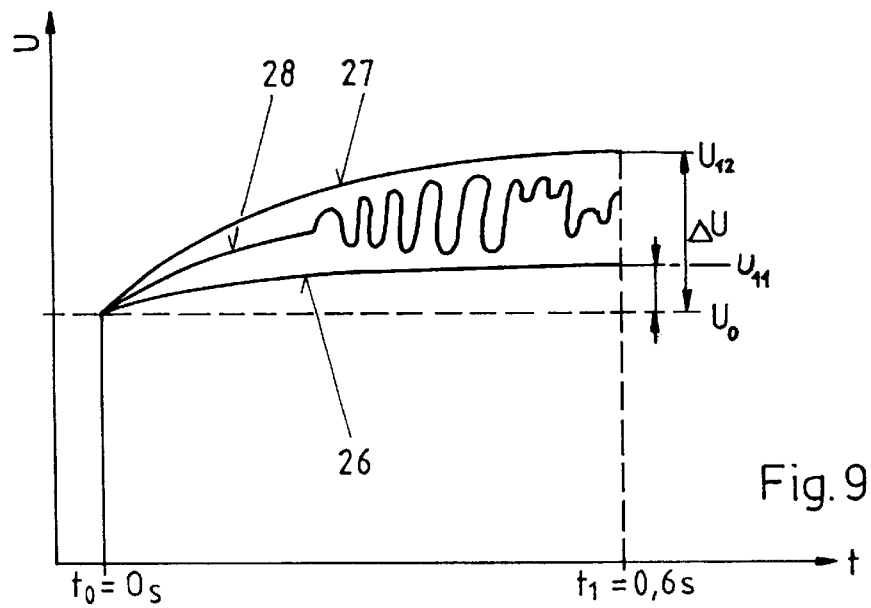
FIG. 9 shows a diagram which indicates the signal voltage of a sensor against time for various operating states.

The diagram in FIG. 9 shows the signal voltage of a sensor 8 against time, said sensor operating on the thermoelectric principle. If the sensor 8 is used for level measurement and is completely immersed in oil, a lower curve 26 is generated. The energization of the sensor 8 begins at time $t_0$. As a result, the temperature of its resistance wire rises. However, this rise is relatively small and the voltage drop across the resistance wire up to the end of energization at time $t_1$, (voltage $U_{11}$) thus also rises only relatively slightly.

If the sensor 8 is out of the oil, it is cooled less and becomes hotter. The upper curve 27 shows that a larger voltage drop (see voltage $U_{12}$ at time $t_1$) then occurs, and it is possible from this to infer this state. To compensate for the effect of the oil temperature, the voltage drop at the beginning of energization is in each case measured first of all, and this is then compared with the voltage drop during energization and, especially, at the end of energization.

The central curve 28 shows that the voltage fluctuates very abruptly between higher and lower values during the operation of the internal combustion engine if air bubbles occur. These rapid fluctuations can be detected, by bandpass filters for example, and recorded in the electronic evaluation system 9, allowing the presence of air bubbles in the oil flow to be inferred from these fluctuations.

What is claimed is:

1. A method for monitoring adequate oil lubrication of an internal combustion engine, in particular that of a vehicle, by a sensor arranged in an oil line of a pressure circulation lubrication system and connected to an electronic evaluation system adapted to generate a warning signal, wherein gas bubbles in the oil flow are detected by the sensor and the electronic evaluation system, and the electronic evaluation system generates a warning signal when the presence of air bubbles exceeds a predetermined level.

2. The method as claimed in claim 1, wherein a sensor operating on the thermoelectric principle is used as the sensor.

3. The method as claimed in claim 2, wherein the sensor has a temperature-dependent wire resistor.

4. The method as claimed in claim 2, wherein the sensor has a thermistor.

5. The method as claimed in claim 1, wherein a capacitive sensor is used as a sensor to detect changes in the dielectric constant of the oil flow passing the sensor.

6. The method as claimed in claim 1, wherein the sensor is arranged at the level of the minimum permissible oil level in an oil pan of the internal combustion engine, and the electronic evaluation system is used to detect when the oil level in the oil pan falls below the minimum with the internal combustion engine stationary, in addition to detecting bubbles with the internal combustion engine running.

7. The method as claimed in claim 6, in which a resistance body in the sensor extends approximately in the vertical direction in the intake line, wherein a constant current is allowed to flow through the resistance body for a defined period of time for each measurement of the oil level, and the voltage drop at the beginning and the end of energization is determined.

8. The method as claimed in claim 6, wherein a constant current is allowed to flow through a resistance body in the sensor for the continuous detection of bubbles, and at the same time the signal fluctuations of the voltage are determined for the purpose of ascertaining the concentration of gas bubbles.

9. The method as claimed in claim 1, wherein the sensor is operating with a dynamic pressure flap which can be deflected by the oil flow is used as the sensor.

10. The method as claimed in claim 1, wherein the sensor is arranged above an approximately horizontal region of the oil line, in the upper region of a flow stagnation space connected in the lower region to the oil line.

11. The method as claimed in claim 10, wherein the flow stagnation space is connected to the oil line via a large cross section in the lower region and, in its upper region, is connected to the oil line in a region of relatively low pressure via a smaller cross section.

12. The method as claimed in claim 1, wherein the sensor is arranged in an oil intake line upstream of an oil pump of the pressure circulation lubrication system.

13. The method as claimed in claim 12, wherein a sensor operating on the thermoelectric principle is used as the sensor.

14. The method as claimed in claim 13, wherein the sensor has a temperature-dependent wire resistor.

15. The method as claimed in claim 13, wherein the sensor has a thermistor.

16. The method as claimed in claim 12, wherein a capacitive sensor is used as a sensor to detect changes in the dielectric constant of the oil flow passing the sensor.

17. The method as claimed in claim 1, wherein the sensor is arranged downstream of the oil pump and downstream of an oil filter arranged downstream of the oil pump.

18. The method as claimed in claim 17, wherein a sensor operating on the thermoelectric principle is used as the sensor.

19. The method as claimed in claim 18, wherein the sensor has a temperature-dependent wire resistor.

20. The method as claimed in claim 18, wherein the sensor has a thermistor.

21. The method as claimed in claim 17, wherein a capacitive sensor is used as a sensor to detect changes in the dielectric constant of the oil flow passing the sensor.

22. An internal combustion engine with a device for monitoring adequate oil lubrication by means of a sensor arranged in an oil line of a pressure circulation lubrication system and connected to an electronic evaluation system adapted to generate a warning signal, wherein the sensor and the electronic evaluation system are designed to detect gas bubbles in the oil flow and to generate a warning signal when the presence of air bubbles exceeds a predetermined level.

23. The internal combustion engine as claimed in claim 22, wherein the sensor is a sensor operating on the thermoelectric principle.

24. The internal combustion engine as claimed in claim 23, wherein the sensor has a temperature-dependent wire resistor.

25. The internal combustion engine as claimed in claim 23, wherein the sensor has a thermistor.

26. The internal combustion engine as claimed in claim 22, wherein the sensor is a capacitive sensor for detecting changes in the dielectric constant of the oil flow passing the sensor.

27. The internal combustion engine as claimed in claim 22, wherein the sensor is arranged at the level of the minimum permissible oil level in an oil pan of the internal combustion engine, and the electronic evaluation system is designed to detect when the oil level in the oil pan falls below the minimum with the internal combustion engine stationary, in addition to detecting bubbles with the internal combustion engine running.

28. The internal combustion engine as claimed in claim 27, in which a resistance body in the sensor extends approximately in the vertical direction in the intake line, wherein the sensor and the electronic evaluation system are designed to detect gas bubbles in the oil flow with the internal combustion engine running and to detect the oil level with the internal combustion engine stationary.

29. The internal combustion engine as claimed in claim 22, wherein the sensor has a dynamic pressure flap which can be deflected by the oil flow.

30. The internal combustion engine as claimed in claim 22, wherein the sensor is arranged above an approximately horizontal region of the oil line, in the upper region of a flow stagnation space connected in the lower region to the oil line.

31. The internal combustion engine as claimed in claim 30, wherein the flow stagnation space is connected to the oil line via a large cross section in the lower region and there is a connection from its upper region to the oil line in a region at relatively low pressure via a smaller cross section.

32. The internal combustion engine as claimed in claim 31, wherein, at one level, the sensor has a resistance wire which extends in a meander shape over the cross section of the oil line.

33. The internal combustion engine as claimed in claim 22, wherein the sensor is arranged in an oil intake line upstream of an oil pump of the pressure circulation lubrication system.

34. The internal combustion engine as claimed in claim 33, wherein the sensor is a sensor operating on the thermoelectric principle.

35. The internal combustion engine as claimed in claim 34, wherein the sensor has a temperature-dependent wire resistor.

36. The internal combustion engine as claimed in claim 34, wherein the sensor has a thermistor.

37. The internal combustion engine as claimed in claim 33, wherein the sensor is a capacitive sensor for detecting changes in the dielectric constant of the oil flow passing the sensor.

38. The internal combustion engine as claimed in claim 22, wherein the sensor is arranged downstream of the oil pump and downstream of an oil filter arranged downstream of the oil pump.

39. The internal combustion engine as claimed in claim 38, wherein the sensor is a sensor operating on the thermoelectric principle.

40. The internal combustion engine as claimed in claim 39, wherein the sensor has a temperature-dependent wire resistor.

41. The internal combustion engine as claimed in claim 39, wherein the sensor has a thermistor.

42. The internal combustion engine as claimed in claim 38, wherein the sensor is a capacitive sensor for detecting changes in the dielectric constant of the oil flow passing the sensor.

* * * * *